US007279570B2

(12) United States Patent
Li et al.

(10) Patent No.: US 7,279,570 B2
(45) Date of Patent: Oct. 9, 2007

(54) NANOSCALE DISCOTIC LIQUID CRYSTALLINE PORPHYRINS

(75) Inventors: Quan Li, Kent, OH (US); Lanfang Li, Kent, OH (US); Antal Jakli, Kent, OH (US); John Harden, Jr., Streetsboro, OH (US)

(73) Assignee: Kent State University, Kent, OH (US)

( * ) Notice: Subject to any disclaimer, the term of this patent is extended or adjusted under 35 U.S.C. 154(b) by 7 days.

(21) Appl. No.: 11/325,478

(22) Filed: Jan. 4, 2006

(65) Prior Publication Data

US 2007/0151600 A1 Jul. 5, 2007

(51) Int. Cl.
*C07D 487/22* (2006.01)
*H01L 51/44* (2006.01)
*H01L 31/042* (2006.01)
*H01L 35/24* (2006.01)
*C09K 19/34* (2006.01)
*C09K 19/32* (2006.01)

(52) U.S. Cl. .................. 540/145; 257/40; 136/263; 438/30; 438/99

(58) Field of Classification Search ........... 252/299.61, 252/299.62; 540/145; 136/263; 438/99, 438/30; 257/40
See application file for complete search history.

(56) References Cited

FOREIGN PATENT DOCUMENTS

| GB | 1458117 | 12/1976 |
|---|---|---|
| JP | 04-120080 | 4/1992 |
| JP | 2002-129051 | 5/2002 |
| JP | 2002-343572 | 11/2002 |
| WO | 97/20846 | 6/1997 |

OTHER PUBLICATIONS

Brian A. Gregg, Marye Anne Fox, Allen J. Bard, "2,3,7,8,12,13,17,18-Octakis(β-hydroxyethyl)porphyrin (Octaethanolporphyrin) and Its Liquid Crystalline Derivatives: Synthesis and Characterization", *Journal American Chemical Society* 1989, 111, pp. 3024-3029.
P. Schouten, J. Warman, M. deHaas, M. Fox, H. Pan, "Charge migration in supramolecular stacks of peripherally substituted porphyrins", *NATURE*, vol. 353, Oct. 24, 1991, pp. 736-737.
B. Patel and K. Suslick, "Discotic Liquid Crystals from a Bis-Pocketed Porphyrin", *Journal American Chemical Society* 1998, 120, pp. 11802-11803.
S. Kumar, "Discotic liquid crystals for solar cells", Current Science, vol. 82, No. 3, Feb. 10, 2002, pp. 256-257.
B. Kippelen, S. Yoo, B. Domercq, C. L. Donley, C. Carter, Wei Xia, B. A. Minch, D. F. O'Brien, N. R. Armstrong, NCPV and Solar Program Review Meeting 2003, NREL/CD-520-33586 pp. 431-434.

(Continued)

*Primary Examiner*—Shean C Wu
(74) *Attorney, Agent, or Firm*—Fay Sharpe LLP

(57) ABSTRACT

Novel nanoscale discotic liquid crystalline porphyrins, methods for their preparation, and device fabrication are disclosed. These compounds are capable of being used as high-efficiency photovoltaic materials, organic semiconducting materials, and organic light emitting materials.

17 Claims, 4 Drawing Sheets

OTHER PUBLICATIONS

Forrest, Stephen R., "The Limits to Organic Photovoltaic Cell Efficiency", *MRS Bulletin*, vol. 30, Jan. 2005, pp. 28-32.

Grätzel, Michael, "Dye-Sensitized Solid-State Heterojunction Solar Cells", *MRS Bulletin*, vol. 30, Jan. 2005, pp. 23-27.

Hatsusaka, K., Ohta, K., Yamamoto, I. and Shirai, H., "Discotic liquid crystals of transition metal complexes, Part 30: spontaneous uniform homeotropic alignment of octakis(dialkoxyphenoxy) phthalocyaninatocopper (ii) complexes", *Journal of Materials Chemistry*, (2001), vol. II, pp. 423-433, © The Royal Society of Chemistry 2000.

Janssen, R. A.J., Hummelen, J.C. and Sariciftci, N.S., "Polymer-Fullerene Bulk Heterojunction Solar Cells", *MRS Bulletin*, vol. 30, Jan. 2005, pp. 33-36.

van de Craats, A. M., Warman, J. M., Hasebe, H., Naito, R. and Ohta, K., "Charge Transport in the Mesomorphic Free-Radical Compound Bis(octakis(dodecyloxy)phthalocyaninato)lutetium(III)", *Journal Phys. Chem. B* (1997), 101, pp. 9224-9232, © 1997 American Chemical Society.

Yang, F., Shtein, M. and Forrest, S. R., "Controlled growth of a molecular bulk heterojunction photovoltaic cell", *Nature Materials*, vol. 4, Jan. 2005, pp. 37-41.

Jiangzong, Li et al., "Synthesis and Mesomorphic behavior of novel discotic meso-tetra (3,4,5-n-trialkoxybenzoylaminophenyl)porphyrins", *Liquid Crystal*, vol. 33, No. 8, pp. 913-919, Aug. 2006 Taylor & Francis Group, Abingdon, GB, XP001246011, ISSN: 0267-8292.

Maeda, Y. et al., "Preliminary Communication. Enantiotropic and monotropic transistions of the discotic mesogen 5, 10, 15, 20-tetrakis (4-n-dodecylphenyl) porphyrin under pressure", *Liquid Crystals*, vol. 25, No. 4, pp. 537-542, Oct. 1998, Lord and Francis, Abingdon, GB, XP000775466, ISSN: 0267-8292.

Shimizu, Y. et al., "Mesomorphic phase transistors of tetraphenylporphyrins with four long aliphatic chains", *Liquid Crystals*, vol. 14, No. 3, pp. 795-805, Jan. 1993, Lord and Francis, Abingdon, GB, XP000383312, ISSN: 0267-8292.

Ohta, K. et al., "Discotic liquid crystals of transition metal complexes. Part 24 Synthesis and mesomorphism of porphyrin derivatives substituted with two or four bulky groups", *Journal of Materials Chemistry*, vol. 8, No. 12, pp. 2637-2650, Dec. 1998, the Royal Society of Chemistry, Cmabridge, GB, XP000804818, ISSN: 0959-9428.

Liu, W. et al., "Synthesis and Characterization of Liquid Crystalline 5, 10, 15, 20-tetrakis(4-n-alkanoyloxphenyl)porphyrins" *Liquids Crystals*, vol. 30, No. 11, pp. 1255-1257, Nov. 2003, Lord and Francis, Abingdon, GB, XP001174710; ISSN: 0267-8292.

Yu, M. et al., "Synthesis and Properties of 5, 10, 15, 20-tetral (4-alkoxy-3-ethyloxy)phenylüporphyrin hydroxylanthanide liquid crystal complexes", *Liquid Crystals*, vol. 32, No. 6, pp. 771-780, Jun. 2005, Lord and Francis, Abingdon, GB, XP001232614, ISSN: 0267-8292.

Ramasseul, R. et al., Phase transitions of long chain esters of meso-tetrakis9para-carboxyphenyl)porphyrin, *Liquid Crystals*, vol. 13, No. 5, pp. 729-733, May 1993, Lord and Francis, Abingdon, GB, XP001082971, ISSN: 0267-8292.

Castella, M. et al., "Fisrt asymmetrically β-tetrasubstituted porphyrin-based discotic lamellar liquid crystal", *Liquid Crystals*, vol. 29, No. 4, pp. 559-565, Apr. 2002, Lord and Francis, Abingdon, GB, XP001082971, ISSN: 0267-8292.

PCT/US2006/48421 International Search Report and Written Opinion mailed Jun. 21, 2007.

NANOSCALE DISCOTIC LIQUID CRYSTALLINE PORPHYRINS

BACKGROUND

The present exemplary embodiments relate to nanoscale discotic liquid crystalline porphyrins. In certain embodiments, they find use as high-efficiency photovoltaic materials, organic semiconducting materials, organic light emitting materials and in solar cell device implementation. However, it is to be appreciated that the present exemplary embodiments are also amenable to other like applications.

In addressing the growing global energy needs, harvesting energy directly from sunlight using photovoltaic technology is a key solution that can provide renewable resources while minimizing detrimental effects on the environment. Silicon based solid state photovoltaic technology is inherently expensive and difficult for mass production, while organic photovoltaic cells have the potential to be produced inexpensively. However, organic semiconductors suffer from other drawbacks, including the scattering of electron/exciton between crystal grain boundaries.

At the present time, the large majority of photovoltaic solar cells are using inorganic semiconductors of doped silicon. The problem with this material is the expensive manufacturing processing, which is essential for good power conversion efficiency (PCE). As an alternate, conjugated polymers have already been studied for photovoltaic applications. The results are promising in terms of ease of processing large films. However, the low exciton diffusion lengths (le≈10 nm) and the low charges carriers mobilities ($\mu \approx 10^{-3}$-$10^{-4}$ cm$^2$/Vs) observed limit the PCE. Another type of semiconductors, showing better mobility values and le (≈1 μm) is the columnar discotic liquid crystals.

A power conversion efficiency of up to about 2% was reported for a self-organized liquid crystal organic solar cell by Schmidt-Mende et al. (Schmidt-Mende, et al., Science, 293, 1119-22 (2001)), who used bilayer of liquid crystalline hexaphenyl-substituted hexabenzocorone (HBCPhC12) as an electron donor and a perylene dicarboxylic acid diimide derivative as an electron acceptor in the active layer of the cell. The HBC-PhC12 has a disc-like structure and forms in room temperature liquid crystalline phase, a discotic liquid, where the molecules self-organize into a columnar structure. This structure forms, because the flat shape of the molecules allows the molecular e-orbital sticking out of the plane of each molecule to form a firm bond between molecules in adjacent layer in the same fashion as in the graphite structure.

Liquid crystals, especially two dimensionally ordered discotic columnar liquid crystals, can form a long range one dimensional self-assembled architecture and can be formed into large area monodomain relatively easily using well established alignment technology developed in the liquid crystal display industry. The present invention relating to the design and synthesis of discotic columnar liquid crystalline porphoryin derivatives is an extension of this idea.

As will be described in detail, the present embodiments provide a broad temperature range discotic columnar phase capable of having a pronounced photovoltage. The materials are capable of being used as photovoltaic materials, organic semiconductors and organic light emitting materials. Although the drawings, discussions and descriptions are mainly directed toward the preparation of the said materials, photovoltaic devices and methods, it is to be understood that the principles of the present invention are applicable to any type of devices that uses a discotic liquid crystal as a photoresponsive semiconductor (For example, photo sensors, electrophotographic receptors, diodes, transistors, memory arrays and the like).

BRIEF DESCRIPTION

In accordance with one aspect of the present exemplary embodiments, there is provided a liquid crystalline porphyrin, having the structure set forth in the claims.

In a second aspect, there is provided, a method for producing the porphyrin.

In a third aspect, there is provided a photovoltaic cell including the porphyrin.

DETAILED DESCRIPTION

There is disclosed herein design and synthesis of nanoscale porphyrin molecules that can self-assemble to columnar mesomorphic structure. These molecules can facilitate charge transport in the direction along the columns, can be processed to form a large area monodomain, can respond to external light irradiation by changing their resistivity, and can convert light to electric energy.

Figure 1:
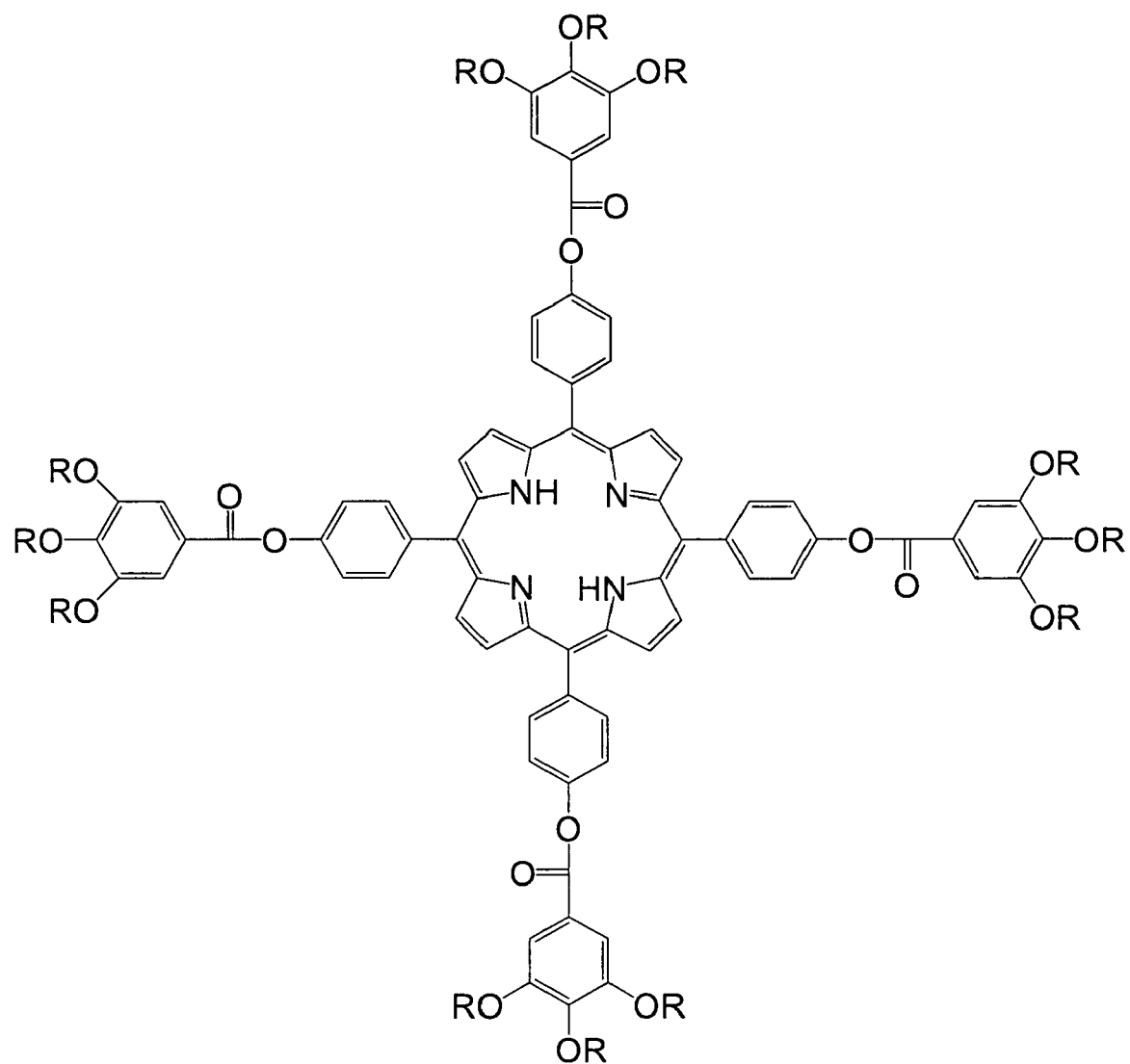
FIG. 1 is the molecular structure of one present embodiment compound.

The structures of the materials are nanoscale porphyrin based molecules with 4 side chain groups of 3,4,5-alkyloxyphenyl connected with a tetraphenylporphyrin core by ester group. The straight or branched alkyl chains R may include one or more —O—, —S—, —CO—, —COO—, —OCO—, —N═N— and/or —C≡C-linkages. In one embodiment, the general structure is shown in FIG. 1.

The general procedure for the preparation of the embodiments of this invention is provided below. In a first method, the target compounds are synthesized by 5,10,15,20-tetra(p-hydroxyphenyl)porphyrin reacting with 3,4,5-tris-alkyloxy benzoic acid or benzoyl chloride in organic media. The intermediate tetra(p-hydroxyphenyl)porphyrin is prepared by cyclocondensation of 4-hydroxy-benzaldehyde and pyrrole.

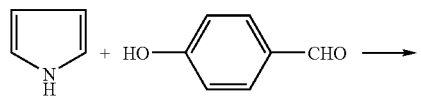

-continued

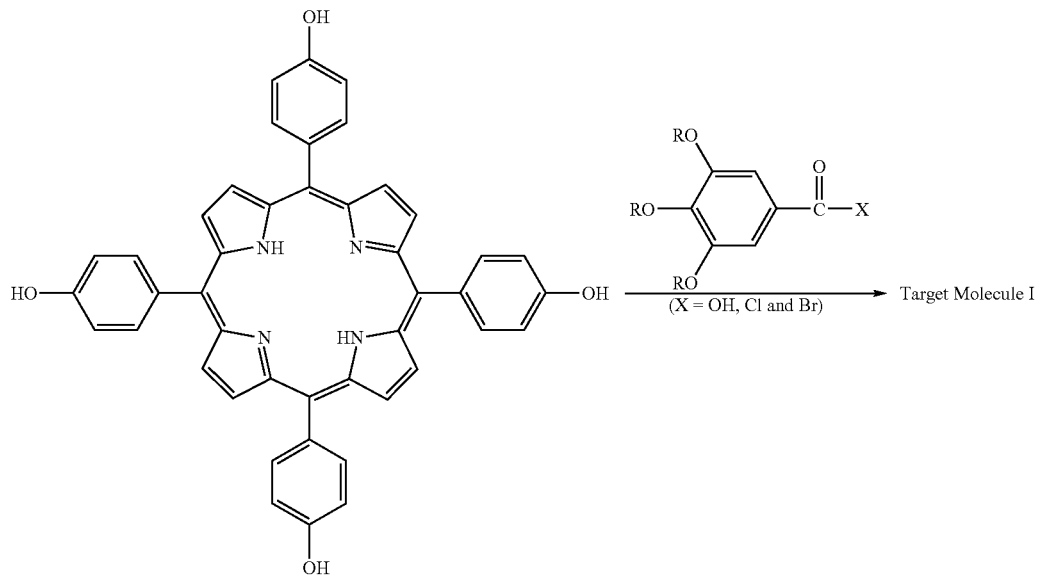
(X = OH, Cl and Br) → Target Molecule I

In a second method, the target compounds are synthesized by cyclocondensation of 3,4,5-tris-alkyloxybenzoic acid 4-formyl-phenyl ester and pyrrole in organic solvent as shown below:

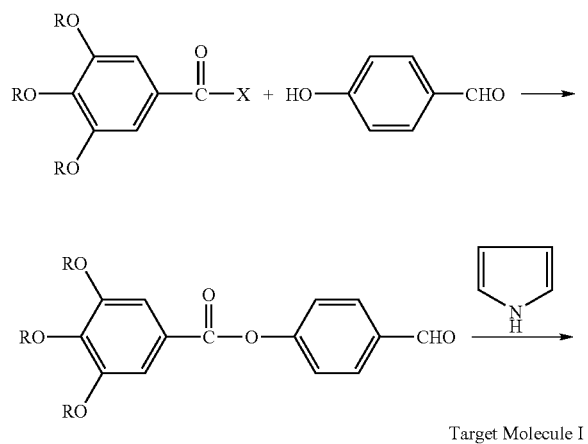
Target Molecule I

In one embodiment, a mixture of 3,4,5-tris-alkyoxy-benzoic acid (0.88 mmol), 5,10,15,20-tetra(p-hydroxyphenyl)porphyrin (0.20 mmol), DCC (dicyclohexyl-carbodidmide, 0.88 mmol) and DMAP (4-dimethylaminopyridine, 0.88 mmol) in organic media was stirred at room temperature or reflux under water free condition for about two days. The resulting reaction mixture was evaporated to dryness under reduced pressure. The residue was purified by flash chromatography on silica gel to afford the claimed target molecule I. The intermediate 3,4,5-tris-alkyoxy-benzoic acid may be synthesized as below. A mixture of methyl 3,4,5-trihydroxybenzoate (0.020 mol), anhydrous potassium hydroxide (0.066 mol) and alkyl bromide (0.066 mol) in DMF (25 mL, dried over molecular sieves) was heated under water free condition and rigorously stirred for 18 hours. It was purified by flash chromatography on silica gel to get 3,4,5-tris-alkyloxy benzoate followed by its hydrolysis to get the 3,4,5-tris-alkyloxy benzoic acid. The intermediate 5,10,15,20-tetra(p-hydroxyphenyl)porphyrin may be synthesized by reacting 4-hydroxy benzaldehyde with pyrrole (well-known Alder condensation reaction).

Suitable organic solvents include, e.g., propionic acid, propionic anhydride, pyrrole, methylene chloride, chloroform, N,N-dimethylformamide, N-methylpyrrolidone, pyridine, triethylamine, ether, tetrahydrofuran, alcohol, ethyl acetate, acetonitrile, ethyl methyl ketone, saturated aliphatic hydrocarbons and aromatic hydrocarbons.

With regard to photovoltaic cells, in general, crystalline molecular organic materials exhibit better transport properties than their polymeric counterparts. However, large single crystals are difficult and costly to process, while polycrystalline materials suffer from the grain boundaries and defects. A disadvantage which can be overcome by utilizing discotic liquid crystals, because their columnar structure resembles the aromatic stacking in single crystalline conductors.

Figure 3:
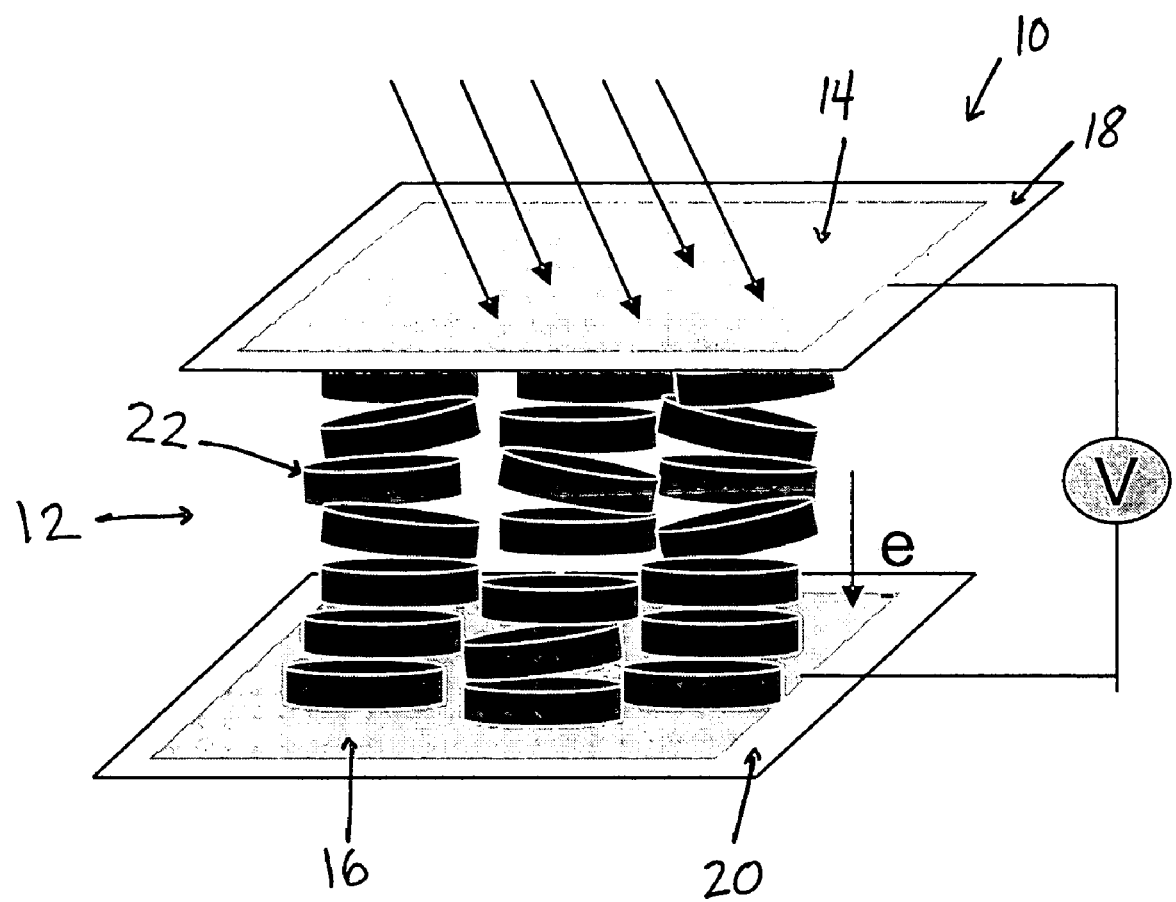
FIG. 3 is general schematic of a photovoltaic cell.

Discotic liquid crystals have recently been used as hole-transporting layer to construct an efficient organic photovoltaic cell. Mesophases formed by these molecules are primarily columnar. In the columnar phase, the discs are stacked one on top of another to form columns, as shown in FIG. 3. Discotic liquid crystals have very high charge carrier mobility in columnar mesophases which offers potential applications as organic charge transport materials in a variety of devices such as one-dimensional conductors, photoconductors, transistors, photovoltaic cells, etc.

Figure 4:
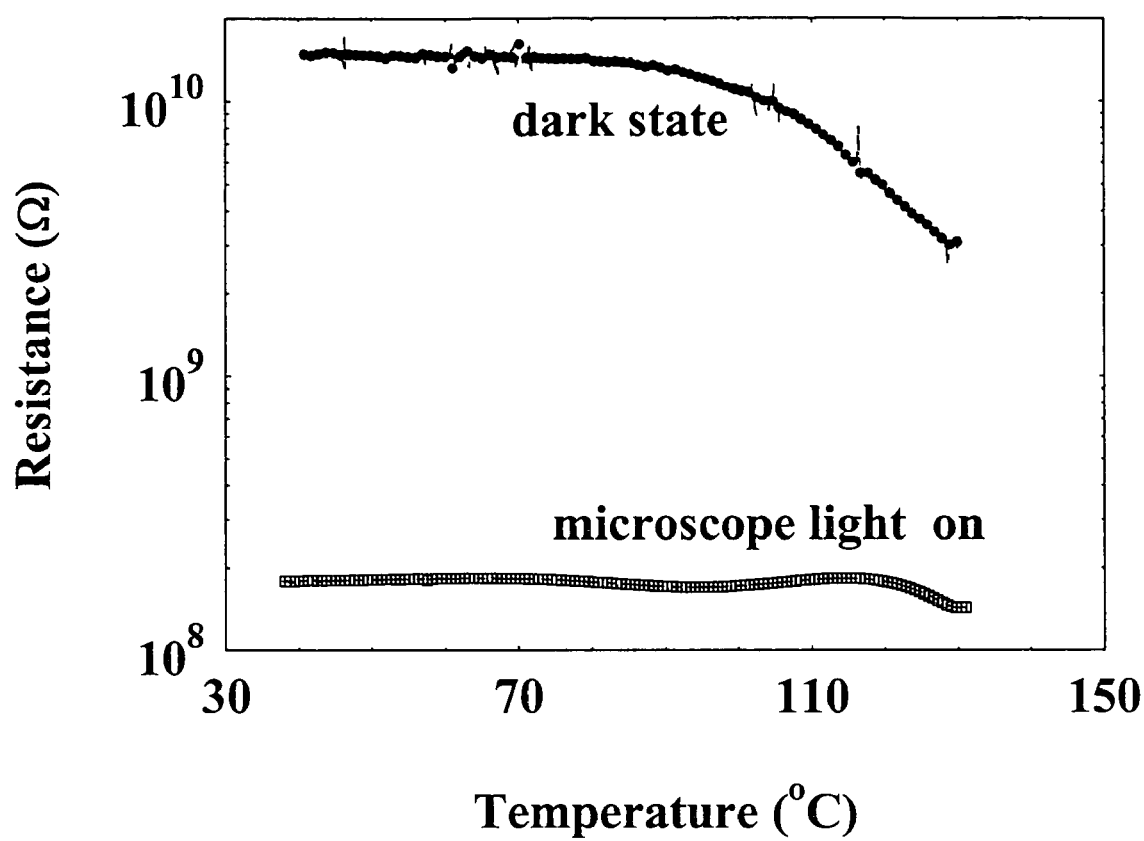
FIG. 4 is temperature dependence of the electric resistance of a 2 μm cell containing the compound in example 1 in homeotropic alignment when measured in dark state, and when under a microscope light illumination (integrated intensity ~10 mW/mm$^2$).

In one embodiment, the present discostic liquid crystals are used to form a photovoltaic cell. As seen in FIG. 4, the structure of a photovoltaic cell 10 includes at least one photoactive semiconductor layer 12 sandwiched between first 14 and second 16 electrodes, the first of which is transparent or substantially transparent. In an embodiment, a p-n junction formed at the interface of two semiconductor layers are positioned between the electrodes. For improved solar cell performance the number If layers and junctions can be multiple. In one embodiment, the electrodes are positioned on first and second substrates 18, 20.

Thus, in one embodiment, substrates which are transparent and have insulating properties, such as a glass plate or a substrate of PET or other organic polymers, can be used as the first transparent substrate 18. The transparent electrode positioned on a surface of the transparent substrate can be composed of common electrodes such as those of indium tin oxide (ITO), tin oxide doped with Sb, F or P, indium oxide doped with Sn, Zn and/or F, antimony oxide, zinc oxide and noble metals. The above transparent electrode layer can be formed by the use of conventional methods, such as the pyrolytic method and the CDV method.

The non-transparent substrate 20 may be a combined substrate/electrode and can be formed of metals such as titanium, aluminum, copper, silver, gold and nickel; or conducting metal oxide, such as zinc oxide, titanium oxide, etc; or conducting polymer such as PPV, PEDOT/PSS, etc. Alternately, a separate electrode can be positioned on a non-conducting substrate.

For example, the electrode material can be any of platinum, rhodium, metallic ruthenium and ruthenium oxide. Further, conductive materials, such as tin oxide, tin oxide doped with Sb, F or P, indium oxide doped with Sn and/or F and antimony oxide, having their surfaces overlaid with the above electrode materials by plating or vapor deposition can also be used as the electrode layer. Still further, common electrodes, such as carbon electrode, can be used for constituting the electrode layer.

As discussed above, the photoactive layer of the photovoltaic cell generally includes two distinct layers forming a p-n junction.

In one embodiment, the photovoltaic cell comprises a photosensitizing agent and a semiconductor. In a specific embodiment, the cell is a dye sensitized device wherein the photoactive layer includes one or more dyes and a discostic liquid crystal material 22 associated with the dye.

The photosensitizing agent can be sorbed (e.g., chemisorbed and/or physisorbed) on the nanoparticles. The photosensitizing agent may be sorbed on the surfaces of the nanoparticles, within the nanoparticles, or both. The photosensitizing agent is selected, for example, based on its ability to absorb photons in a wavelength range of operation (e.g., within the visible 0 spectrum), its ability to produce free electrons (or electron holes) in a conduction band of the nanoparticles, and its effectiveness in complexing with or sorbing to the nanoparticles. Suitable photosensitizing agents may include, for example, dyes that include functional groups, such as carboxyl and/or hydroxyl groups.

Examples of dyes include black dyes (e.g., tris(isothiocyanato)-ruthenium (II)-2,2':6',2''-terpyridine-4,4',4''-tricarboxylic acid, tris-tetrabutylammonium salt), orange dyes (e.g., tris(2,2'-bipyridyl-4,4'-dicarboxylato) ruthenium(II) dichloride, purple dyes (e.g., cis-bis(isothiocyanato)bis-(2,2'-bipyridyl-4,4'-dicarboxylato)-ruthenium (II)), red dyes (e.g., an eosin), green dyes (e.g., a merocyanine) and blue dyes (e.g., a cyanine). Examples of additional dyes include anthocyanines, perylenes, porphyrins, phthalocyanines, squarates, and certain metal-containing dyes.

The discotic liquid crystal is sandwiched in between these two substrates and aligned homeotropically (with the liquid crystal molecules parallel to the substrates and the stacked columns perpendicular to the substrates). With further detail, the two electrodes are glued or otherwise attached and sealed to form a cell. Depending on the method of filling the cell, a small slit may be maintained for liquid crystal uptake. A typical gap thickness between the two electrodes is about 1-8 μm. The liquid crystal is then deposited inside the cell using known methods. After dryness of the film, the other electrode is laminated on top of the film to form a cell.

In one embodiment, the discotic liquid crystal as the hole-transporting layer and a photosensitizing agent as electron transporting layer may be prepared in a solvent and spin-coated onto an indium tin oxide electrode. Suitable solvents may be, e.g., water, alcohols, oligoethers, carbonates such as propione carbonate, phosphoric esters, dimethylformamide, dimethyl sulfoxide, N-methylpyrrolidone, N-vinylpyrrolidone, sulfur compounds such as sulfolane 66, ethylene carbonate, acetonitrile and γ-butyrolactone.

Alternately, in another embodiment, the discotic liquid crystal may be heated to melting inside a vacuum chamber. The cell is then placed in the vacuum chamber to remove any air inside the cell. To fill the cell, the opening slit of the cell is dipped into the melted material. The vacuum level is then slowly reduced to allow the cell to uptake the material. Of course, other methods of filling the cell are also possible.

In specific embodiments, the photovoltaic device is composed of an ITO coated transparent electrode and an aluminum, copper, silver or gold coated reflective electrode. In specific embodiment of the invention, the transparent substrate can be glass or plastic. In specific embodiment of the invention, the alignment of the materials is homeotropic.

With patterned and individually addressable electrode on certain substrate, the claimed liquid crystal material could be prepared in the form of a film on top of these patterned electrode substrate in the same way as mentioned. The photosensitive resistance plus the photo-voltage produced at different site of the substrate can map the intensity of the object in front of the film. In this way, the liquid crystal material can be used as a photo-image receiver.

In one embodiment, a small area solar cell can act as a simple photosensor in conjugation with a Schmidt trigger circuit, which can set a tunable threshold voltage for detection and act as a photosensor.

EXAMPLES

In accordance with the present embodiments, a series of nanoscale porphyrins was synthesized and characterized.

Example 1

5,10,15,20-tetra{p-[3',4',5'-tris-dodecyloxybenzoyloxy]phenyl}porphyrin: The structure is shown below.

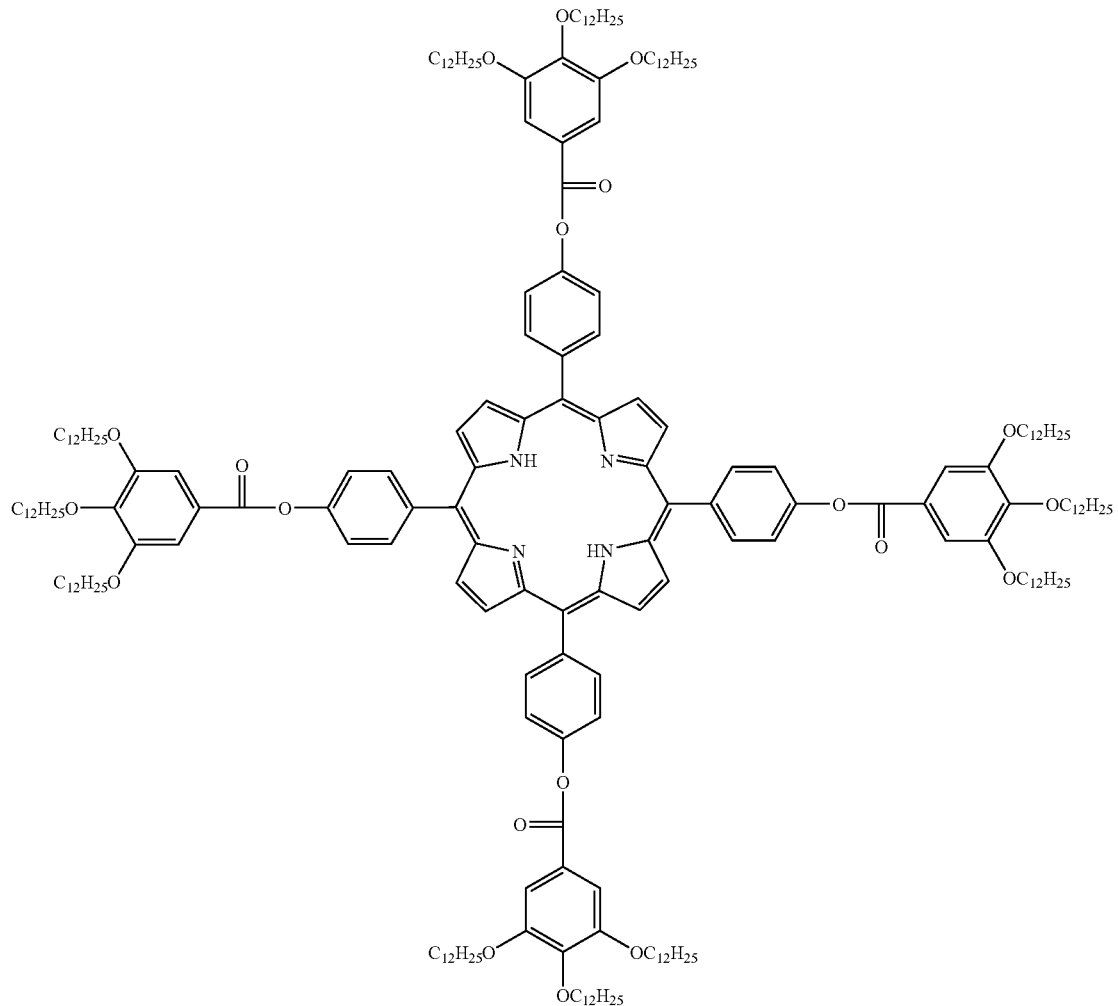

The compound was initially crystal when first processed from solution, then on the first heating cycle, the crystal melts into a columnar mesophase at 77° C. with ΔH=23.422 kCal/mol, then melt into an isotropic liquid at 154.7° C. with ΔH=4.587. On cooling, the material goes to a discotic nematic phase at 143.358° C. with ΔH=0.927 kCal/mol, then from this discotic nematic phase into discotic columnar at 142.216° C. with ΔH=3.913 kcal/mol. The existence of nematic phase facilitates the alignment process of the material because its fluidity enables director orientation.

Figure 2:
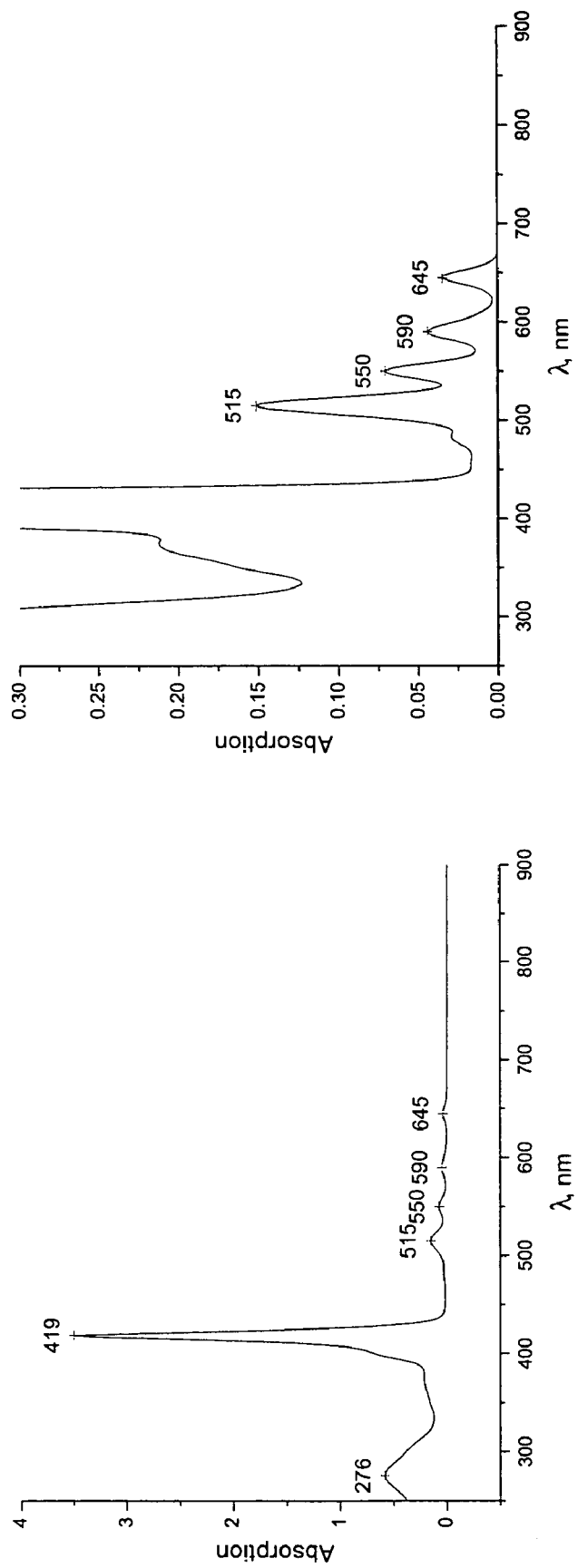
FIG. 2 is UV-visible absorption of the compound.

Its UV-visible absorption spectrum was measured (FIG. 2). The very strong absorption at 419 nm enables it to be a very efficient absorber for blue photons. The absorption peak at 515 nm, 550 nm, 590 nm, 645 nm enables this material as a good absorber for a large spectrum of the sunlight. FIG. 4 is temperature dependence of the electric resistance of a 2 μm cell containing the compound in example 1 in homeotropic alignment when measured in dark state, and when a microscope light (integrated intensity ~10 mW/mm$^2$, which approximately mimics light intensity in normal daylight) illuminated the cell.

In a reverse process, one can use this material as a light emitter for the above said wavelengths. In this process electric current is pumped through the material, which in turn emits light in the wavelengths corresponding to the maxima of their absorption spectra.

Example 4

5,10,15,20-tetra{p-[3',4',5'-tris-dodecyloxybenzoyloxy]phenyl}porphyrin

Example 5

5,10,15,20-tetra{p-[3',4',5'-tris-undecyloxybenzoyloxy]phenyl}porphyrin

Example 6

5,10,15,20-tetra{p-[3',4',5'-tris-tetradecyloxybenzoyloxy]phenyl}porphyrin

Example 7

5,10,15,20-tetra{p-[3',4',5'-tris-hexadecyloxybenzoyloxy]phenyl}porphyrin

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

What is claimed is:

1. A liquid crystalline porphyrin, having the structure I below:

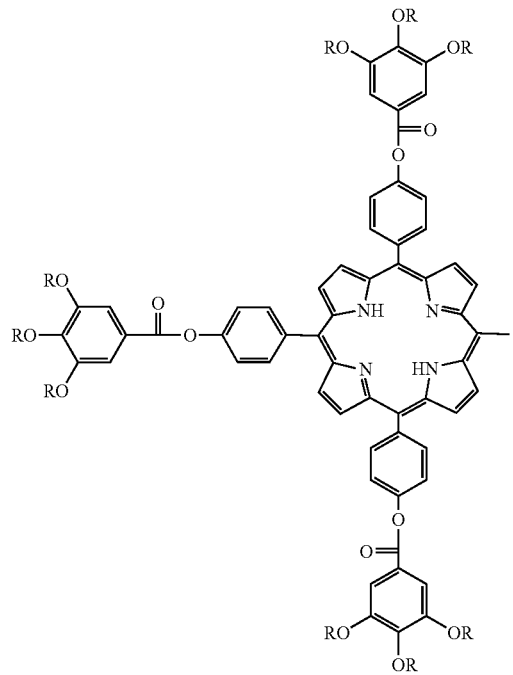

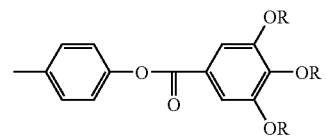

wherein R is a straight chain or branched alkyl which may include at least one linkage of the type —O—, —S—, —CO—, —COO—, —OCO—, —N=N—, or —C≡C—.

2. A porphyrin according to claim 1, wherein said porpyrin comprises at least one of: 5,10,15,20-tetra{p-[3',4',5'-tris-dodecyloxybenzoyloxy]phenyl}porphyrin; 5,10,15,20-tetra{p-[3',4',5'-tris-undecyloxybenzoyloxy]phenyl}porphyrin; 5,10,15,20-tetra {p-[3',4',5'-tris-tetradecyloxybenzoyloxy]phenyl}porphyrin; and 5,10,15,20-tetra{p-[3',4',5'-tris-hexadecyloxybenzoyloxy]phenyl}porphyrin.

3. A method for producing the porphyrin of claim 1, comprising the following synthesis steps:

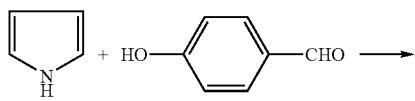

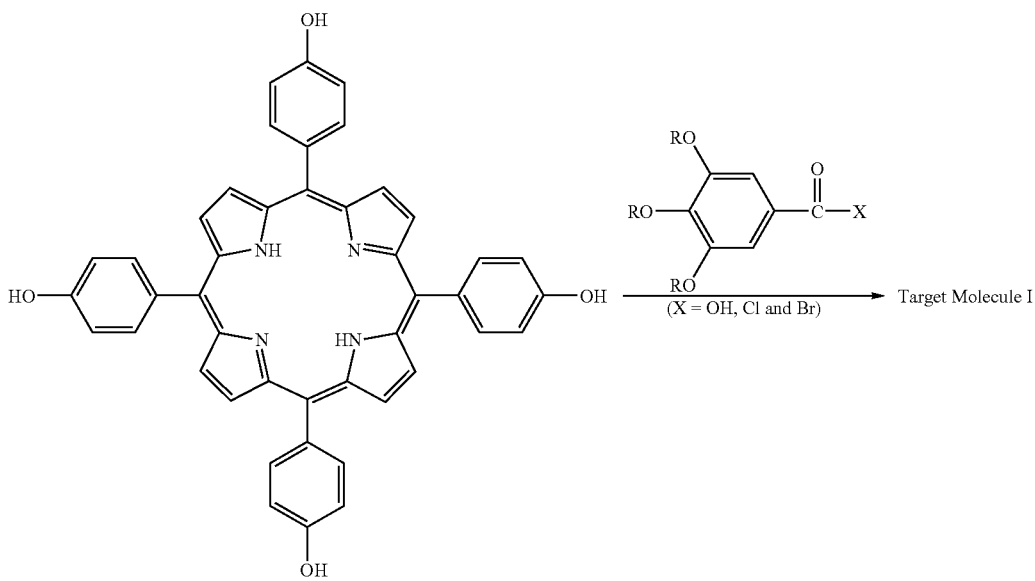

4. A method according to claim 3, wherein said synthesis is conducted in an organic solvent.

5. A method according to claim 4, wherein said organic solvent comprises at least one of propionic acid, propionic anhydride, pyrrole, methylene chloride, chloroform, N,N-dimethylformamide, N-methylpyrrolidone, pyridine, triethylamine, ether, tetrahydrofuran, alcohol, ethyl acetate, acetonitrile, ethyl methyl ketone, saturated aliphatic hydrocarbons and aromatic hydrocarbons.

6. A method for producing the porphyrin of claim 1, comprising the following synthesis steps:

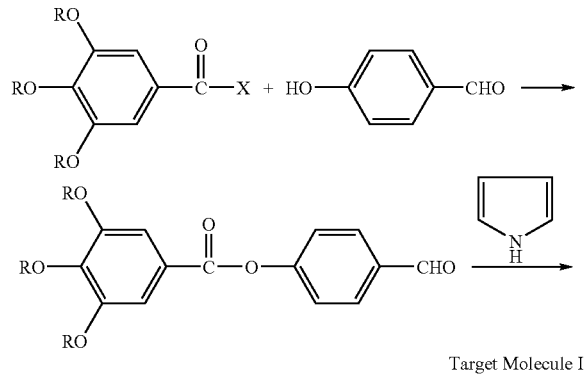

Target Molecule I where X is OH, Cl or Br.

7. A method according to claim 6, wherein said synthesis is conducted in an organic solvent.

8. A method according to claim 7, wherein said organic solvent comprises at least one of methylene chloride, chloroform, ether, tetrahydrofuran, pyrrole, propionic acid, propionic anhydride, pyridine, triethylamine, N, N-dimethylformamide, N-methylpyrrolidone, alcohol, ethyl acetate, acetonitrile, ethyl methyl ketone, saturated aliphatic hydrocarbons and aromatic hydrocarbons.

9. A photovoltaic cell including the porphyrin of claim 1.

10. A photovoltaic cell according to claim 9, wherein said cell comprises a first transparent electrode, a second electrode, and the porphyrin positioned between said first and second electrodes.

11. A photovoltaic cell according to claim 10, wherein said first electrode is an indium tin oxide electrode, wherein said electrode is coated on a glass or plastic substrate.

12. A photovoltaic cell according to claim 10, wherein said second electrode comprises aluminum, copper, silver and/or gold.

13. A photovoltaic cell according to claim 10, further comprising a photosensitizing agent.

14. A photo-sensitive electric resistor comprising the porphyrin of claim 1.

15. An organic light emitter comprising the porphyrin of claim 1.

16. A method for producing a photovoltaic cell, including the steps of:
 a) providing a first transparent electrode and a second electrode;
 b) positioning the liquid crystal porpyrin of claim 1 between said first and second electrodes; and
 c) aligning said porphyrin homeotropically.

17. A method according to claim 16, further comprising:
 a) sealing the two electrodes together while maintaining a liquid crystal uptake opening between the two;
 b) heating said porphyrin in a vacuum chamber to melt it;
 c) placing the cell in said vacuum chamber to remove air from the cell;
 d) Dipping the cell opening into the melted porphyrin; and
 e) reducing the vacuum level in said vacuum chamber to allow the cell to uptake the melted porphyrin.

* * * * *